(12) United States Patent
Dycher et al.

(10) Patent No.: US 11,986,577 B2
(45) Date of Patent: May 21, 2024

(54) WICKING DEVICE FOR EVAPORATION OF A FRAGRANCE WITH A WICK HOLDER

(71) Applicant: CTR, LDA, Samora Correia (PT)

(72) Inventors: David Dycher, Port Erin (GB); Pedro Queiroz Vieira, Belas (PT)

(73) Assignee: CTR, LDA, Samora Correia (PT)

( * ) Notice: Subject to any disclaimer, the term of this patent is extended or adjusted under 35 U.S.C. 154(b) by 1162 days.

(21) Appl. No.: 16/310,257

(22) PCT Filed: Jun. 16, 2016

(86) PCT No.: PCT/EP2016/001007
§ 371 (c)(1),
(2) Date: Dec. 14, 2018

(87) PCT Pub. No.: WO2017/215727
PCT Pub. Date: Dec. 21, 2017

(65) Prior Publication Data
US 2019/0117816 A1    Apr. 25, 2019

(51) Int. Cl.
*A01M 1/20* (2006.01)
*A61L 9/03* (2006.01)
(Continued)

(52) U.S. Cl.
CPC ........... *A61L 9/037* (2013.01); *A01M 1/2044* (2013.01); *A01M 1/2077* (2013.01); *A61L 9/127* (2013.01); *F23D 3/24* (2013.01); *A61L 2209/133* (2013.01)

(58) Field of Classification Search
CPC .............. A01M 1/2022; A01M 1/2044; A01M 1/2061; A01M 1/2077; A61L 9/037
(Continued)

(56) References Cited

U.S. PATENT DOCUMENTS 3,028,100 A * 4/1962 Russo ................... A45D 34/04
239/47
3,724,756 A * 4/1973 Maltenfort ............ B65D 51/24
239/47
(Continued)

FOREIGN PATENT DOCUMENTS

CN          103096940 A      5/2013
EP          1331014 A2       7/2003
(Continued)

*Primary Examiner* — David J Parsley
(74) *Attorney, Agent, or Firm* — Laurence A. Greenberg; Werner H. Stemer; Ralph E. Locher

(57) ABSTRACT

A device for the release, in particular for evaporation, of volatile substances such as fragrances or active substances, has a container for a substance to be released. At least one wick as a capillary element is in contact with the substance to be released and at least partially in the receptacle and has a substance release region. The wick, preferably its substance release region, is assigned a heating element, preferably an electrical heating element. The wick is assigned a squeezing device with a squeezing element, by which a squeezing region of the wick can be subjected to a squeezing force and/or can be compressed, in particular for a defined short period of time and/or temporarily. A defined amount of substance, in particular at least the substance collected in the squeezing region, can be conveyed with a boost in the direction of the substance release region.

34 Claims, 5 Drawing Sheets

(51) Int. Cl.
*A61L 9/12* (2006.01)
*F23D 3/24* (2006.01)

(58) Field of Classification Search
USPC .............................................................. 43/1
See application file for complete search history.

(56) References Cited

U.S. PATENT DOCUMENTS

| | | | | |
|---|---|---|---|---|
| 3,730,434 | A * | 5/1973 | Engel | A01M 1/2055 |
| | | | | 239/47 |
| 4,136,825 | A | 1/1979 | Mack et al. | |
| 4,742,960 | A | 5/1988 | Bustillo et al. | |
| 4,847,192 | A | 7/1989 | Fujimoto et al. | |
| 6,896,196 | B2 | 5/2005 | Vieira | |
| 7,424,979 | B1 * | 9/2008 | Chen | B05B 17/0646 |
| | | | | 239/102.1 |
| 9,370,594 | B2 | 6/2016 | Gasper et al. | |
| 2003/0132308 | A1 | 7/2003 | Vieira | |
| 2005/0037307 | A1 | 2/2005 | Decker et al. | |
| 2008/0253755 | A1 * | 10/2008 | Smith | A61L 9/037 |
| | | | | 392/386 |
| 2009/0232581 | A1 * | 9/2009 | Tong | B43K 8/06 |
| | | | | 401/101 |

FOREIGN PATENT DOCUMENTS

| | | |
|---|---|---|
| EP | 1839684 A1 | 10/2007 |
| WO | 9858692 A1 | 12/1998 |
| WO | 2004030708 A1 | 4/2004 |
| WO | 2006113253 A1 | 10/2006 |
| WO | 2008066384 A2 | 6/2008 |
| WO | 2012009017 A1 | 1/2012 |

* cited by examiner

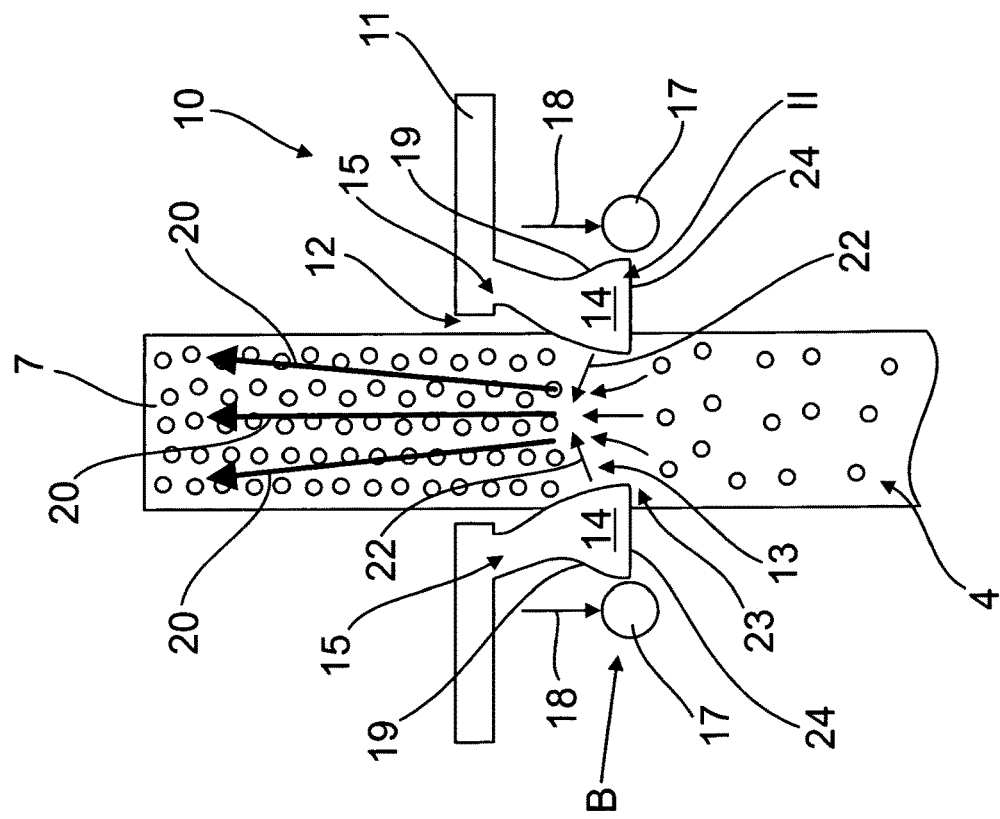
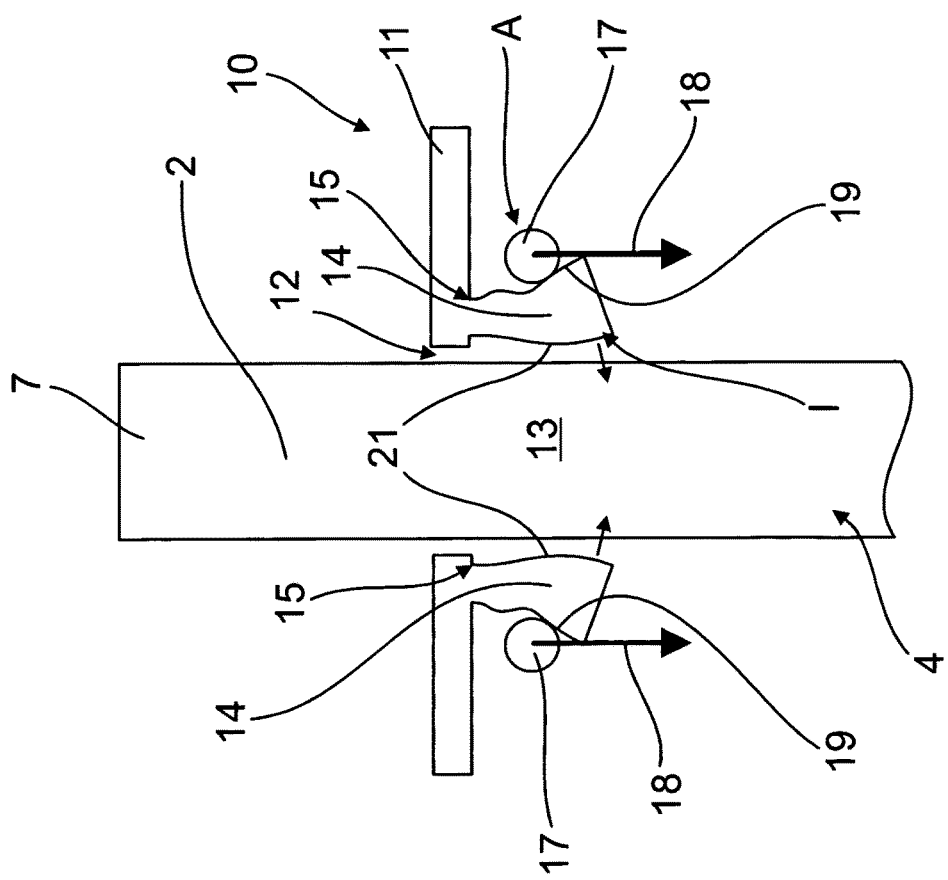
Fig. 4b
Fig. 4a

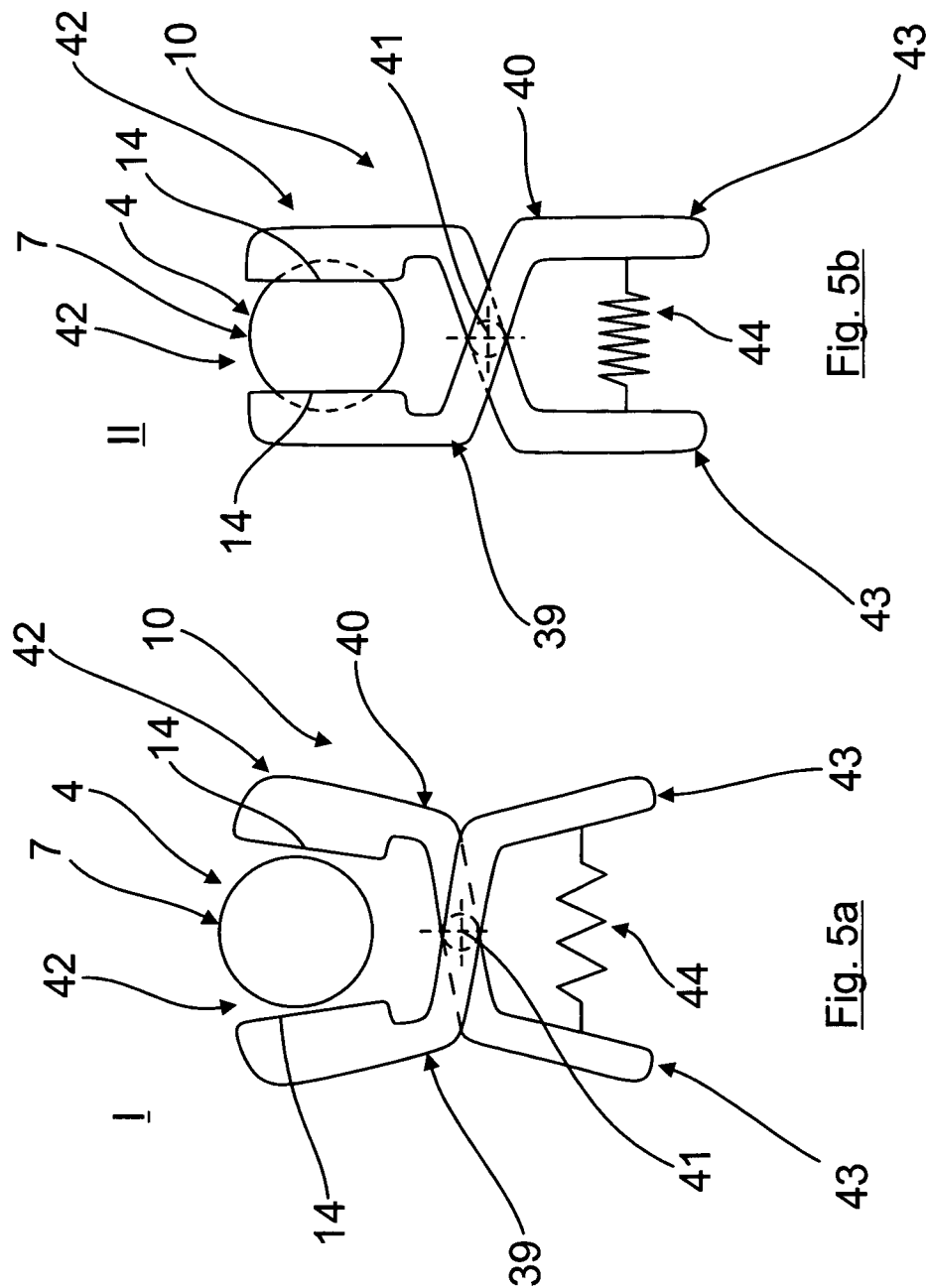

WICKING DEVICE FOR EVAPORATION OF A FRAGRANCE WITH A WICK HOLDER

BACKGROUND OF THE INVENTION

Field of the Invention

The invention relates to a device for dispensing, in particular for vaporizing, volatile substances, in particular fragrances and/or active agents. The device has a container in which a substance to be dispensed is received, at least one wick as capillary element which is in contact with the substance to be dispensed, is arranged at least in regions in the container and comprises a substance dispensing region. It is provided in a preferred manner that at least one heating element, preferably an electrical heating element, is assigned to the wick, preferably to the substance dispensing region of the wick. In addition, the invention relates to a squeezing device for the wicking device and to a method for dispensing, in particular for vaporizing, volatile substances.

Devices for dispensing, in particular for vaporizing, volatile substances, in particular fragrances and/or active agents, are known generally and as a rule include a container in which a substance to be dispensed is received. A wick, which projects beyond the container by way of a free wick end and is in contact with the substance to be dispensed in such a manner that said substance is conveyed in the direction of the free wick end by means of the capillary action of the wick, is arranged in the container as a capillary element. The free wick end regularly has assigned thereto a heating element, in particular an electrical heating element, by means of which the free wick end may be subjected to heat in order to be able to dispense or vaporize the substance accumulating in the free wick end even quicker to the surrounding area. Such a design is disclosed, for example, in WO 98/58692 A1. In order to be able to adjust the degree of vaporization and consequently the vaporization performance, said WO 98/58692 A1 further provides mounting the container together with the wick so as to be vertically adjustable in the housing of the device such that the relative position of the wick is modifiable with respect to the heating device.

With such a design, it is possible to influence the vaporization rate and consequently the dispensing rate of the substance to be dispensed over a longer period. If, however, there is a need for a brief, boost-like increase in the substance dispensing rate or vaporization rate, such a device is then little suited or not suited at all for this, in particular also because it takes a relatively long time after a successful relative adjustment for the dispensing rate of the sluggish system per se to increase.

Consequently, it is the object of the present invention to create a device for dispensing, in particular for vaporizing, volatile substances, in particular fragrances and/or active agents, by means of which a brief, boost-like increase in the dispensing rate of the substance to be dispensed is made possible in a simple and functionally reliable manner.

SUMMARY OF THE INVENTION

Said object is achieved with the features of the independent patent claims. Advantageous designs are the object of the subclaims which are dependent thereon.

There is proposed a device for dispensing, in particular for vaporizing, volatile substances, in particular fragrances and/or active agents, having a container in which a substance to be dispensed is received. Additionally provided is at least one wick as capillary element, which is in contact with the substance to be dispensed, is arranged at least in regions in the container and comprises a substance dispensing region, preferably a free wick end which projects beyond the container as substance dispensing region, wherein it is provided in a preferred manner that at least one heating element, preferably an electrical heating element, is assigned to the substance dispensing region.

According to the invention, a squeezing device with at least one boosting or squeezing element (designated below as squeezing element) is assigned to the wick, by means of which a, preferably elastically deformable, squeezing region of the wick, is actable upon and/or compressible, in particular briefly or for a defined short period and/or transiently, by means of a clamping or squeezing force. It is provided in a preferred manner in this connection that the squeezing region of the wick, after having been acted upon by means of squeezing force or after being compressed, returns into its original form again, in a preferred manner slowly in contrast to the squeezing deformation. As a result, a defined substance quantity, in particular at least the substance accumulated in the squeezing region, is conveyed in a boost-like manner substantially in the direction of the substance dispensing region. This means in other words that an increased substance quantity, compared to a non-compressed or squeezed state, is conveyed in the direction of the substance dispensing region in order to achieve a briefly increased and consequently boost-like dispensing of a larger substance quantity there.

A further advantage of such a squeezing device is that the boost quantity can be controlled here in a simple manner as a result of the squeezing force applied, in a preferred manner also in dependence on the specific design of the wick, in particular on the specific design of the wick in the squeezing region. In order to ensure that the wick or in particular the squeezing region of the wick is also able to return into its original form again after actuation of the squeezing device or after being acted upon by means of a squeezing force, it is particularly advantageous when at least the squeezing region of the wick is realized as an elastically deformable region.

The term "substance to be dispensed" is to be understood here specifically in a broad sense and includes all substances which can be conveyed by means of the capillary action of a wick as capillary element. Along with liquid substances, these can also be specifically gel-like or other suitable substances.

In principle, in dependence on the respective wick design and/or in dependence on the respective design of the container, each wick region can be realized as a wick squeezing region insofar as, when it is compressed or squeezed together in the desired manner, the boost-like, brief increase and concentration of the substance to be dispensed is made possible in the respective substance dispensing region. According to a particularly preferred specific design, the substance dispensing region is formed by a free wick end which projects beyond the container, in particular beyond a container opening, in the event of a heating element being provided, the at least one heating element is then assigned to said free wick end.

The squeezing device can be assigned to the wick in the event of a free wick end projecting beyond the container or the container opening in principle at any suitable point, in particular outside or inside the container. According to a particularly preferred design, it is, however, provided in this case that the squeezing device is assigned to the wick in the region of the free wick end such that the squeezing device can be arranged outside the container and/or the, preferably elastically deformable, squeezing region of the wick is realized in the region of the free wick end. This ensures in a particularly simple and functionally reliable manner that when the squeezing device is actuated, a defined or increased substance quantity, in particular the substance accumulated in the squeezing region, is displaced substantially in the direction of the free wick end. If said wick end has assigned thereto, for example, a heating element, the substance to be dispensed is vaporized in the desired boost-like manner.

According to a further particularly preferred design of the device according to the invention, it is provided that the at least one squeezing element is arranged on the squeezing device so as to be displaceable between a home position, in which the at least one squeezing element does not compress the squeezing region or does not compress it significantly (that is to say no such squeezing force is applied which leads to a boost-like increase in substance quantity in the substance dispensing region), and a squeezing position. As a result, the at least one squeezing element is displaceable in the direction of the squeezing region of the wick when the squeezing device is actuated. Particularly preferred, in this connection, is a design where the at least one squeezing element is hinged on the squeezing device in such a manner so as to be pivotable that it is pivotable between a home position and a squeezing position and when the squeezing device is actuated is pivotable in the direction of the squeezing region of the wick. Such a pivotable arrangement of the at least one squeezing element about a pivot axis can be achieved in a particular simple manner as regards production and manufacture, in particular also in conjunction with a particularly compact design.

Particularly preferred, in this connection, is a design where the at least one squeezing element enables air to flow around the wick in the home position. This is achieved in a particularly simple manner as a result of the at least one squeezing element being at a defined gap clearance from the squeezing region of the wick in the home position.

According to a further particularly preferred design of the present inventive concept, when the squeezing device is actuated, the at least one squeezing element, (in particular the at least one squeezing element which is connected to the squeezing device so as to be pivotable, in the state thereof pivoted into the squeezing position), can abut against the wick squeezing region in a bearing connection by way of a squeezing element contact surface. The at least one squeezing element, in this case, can be arranged so as to be displaceable, in particular pivotable, in such a manner and/or the squeezing element contact surface can comprise such a design and form that the wick in the wick squeezing region is acted upon by means of a force or force component, which acts substantially in the direction of the substance dispensing region, in particular is acted upon by means of a force or force component aligned in the direction of a free wick end and/or obliquely upwardly in order to ensure that the substance is displaced upward substantially in the direction of the substance dispensing region or, in the specific example case, in the direction of the free wick end. For example, such a force or force component can be aligned at an angle of between 30° and 75° in relation to a horizontal.

As an alternative to this or in addition to it, the squeezing element contact surface can comprise such a design and form that the wick, in the wick squeezing region and when viewed in the direction of the wick vertical axis, comprises a form which tapers at least in regions toward the direct contact region, in particular a form which tapers in a cone-like and/or obliquely downward manner at least in regions toward the direct contact region, in the direct contact region between the squeezing element contact surface and the wick when the squeezing device is actuated. Such a design ensures in a simple manner that a force or force component acts substantially in the direction of the substance dispensing region, in particular, for example, in the direction of the free wick end and/or that the substance accumulated in the squeezing region is displaced in the desired manner in the direction of the substance dispensing region or, in the specific design, toward the free wick end in order to generate the desired boost effect there.

The boost-like, brief conveying and concentration of the substance to be dispensed in the substance dispensing region can also be further supported, where applicable, as a result of the wick region connecting in the direction of the wick vertical axis below the direct contact region between the at least one squeezing element and the wick widening in a step-like or edge-like manner. In conjunction with such an embodiment, it is then ensured that a constriction is realized in the region of the step-like or edge-like widening which, when the squeezing device is actuated, favors the displacement or conveying of the substance to be dispensed in the direction of the wick region which connects thereto above and widens in a cone-like manner.

In principle, there are numerous possibilities to design the squeezing element contact surface in order to obtain the above-described measures and effects. However, squeezing element contact surfaces which comprise a concave or convex form or even a form that extends in a rectilinear manner have proved to be particularly suitable.

In order to achieve a return or a transition into the normal state again after a boost, the squeezing device can comprise a restoring device, by means of which the at least one squeezing element can be displaced from the squeezing position back into the home position. In this case, the restoring device can be formed, for example, by a restoring element, by means of which the at least one squeezing element is displaceable from the squeezing position back into the home position. According to a preferred specific design for this purpose, it can be provided, for example, that the restoring element is at the same time also a constituent part of an actuating device of the squeezing device, which is to be described in more detail below, by means of which the at least one squeezing element, when the actuating device is actuated, is displaceable from the squeezing position back into the home position. This can be effected actively, for example, by an operator.

If the return of the squeezing element is effected too abruptly, the squeezing region of the wick is released too quickly such that it returns too quickly into its original form again, which entails a certain risk of the substance displaced in the direction of the substance dispensing region then being sucked back up. In order to prevent this, wicks can be used, for example, which are designed at least in the squeezing region such that after a successful squeezing and release of the squeezing region, they do not return abruptly, but only gradually or slowly into their original form again. As an alternative to this or in addition to it, measures can also be provided which dampen or slow the return of the squeezing element from the squeezing position into the rest position in such a manner that the squeezing element does not release the squeezing region too abruptly and jerkily. This can be effected, for example, by providing a soft brake, for example in the connecting or hinging region of the squeezing element. This can also be achieved, however, in a particularly advantageous manner with an embodiment which is particularly preferred for other reasons, in particular from a production and manufacturing point of view, according to which the restoring element, as an alternative or, where applicable, also in addition to return displacement by means of an actuating device, is formed by an elastically resilient element which is compressible when the at least one squeezing element is transferred into the squeezing position and which, when there is a lack of force application by the squeezing device and/or the squeezing device is not actuated, the at least one squeezing element moves automatically from the squeezing position back into the home position. Said elastically resilient element can be formed, for example, by an elastically resilient squeezing region of the wick such that it then also forms a constituent part of the squeezing device in a dual function. As an alternative to this or in addition to it, this can also, however, be achieved with a specific embodiment where the restoring device, in particular a restoring element of the restoring device, is realized by an elastically resilient connection between the at least one squeezing element and the squeezing device, where the at least one squeezing element—pre-tensioned in the direction of the home position—is connected in an elastically resilient manner to the squeezing device, in particular is pivotably hinged. The connection or pivotable hinging is effected, in this case, preferably in such a manner that the at least one squeezing element, when there is a lack of force application by the squeezing device and/or the squeezing device is not actuated, moves automatically from the squeezing position back in the direction of the home position.

For a particularly advantageous assignment and positioning of the wick in connection with the squeezing device, it is provided in a preferred manner that the squeezing device comprises a wick through opening, through which the wick is guidable and in the region of which is arranged the at least one squeezing element, correspondingly assigned to the squeezing region of the wick. To act with force in a particularly preferred uniform manner on the wick squeezing region, it is provided in a preferred manner that the at least one squeezing element is arranged at least in regions around the wick through opening and consequently around the squeezing region of the wick.

A simpler design as regards production and manufacturing is distinguished in particular as a result of the wick through opening being realized in a, preferably plate-shaped and/or ring-shaped, holder of the squeezing device, the at least one squeezing element being arranged, in particular is pivotably hinged there, at least in regions around the wick through opening and consequently around the squeezing region of the wick on the holder of the squeezing device.

According to a particularly preferred specific design which allows force to be applied onto the wick squeezing region in a manner that is particularly advantageous and easy to control, the squeezing element is formed by multiple clamping jaws which are displaceable, in particular pivotable about a pivot axis. In a particularly preferred manner, the multiple clamping jaws, in this connection, are pivotably mounted, preferably in such a manner that they are pivotable about a vertical axis which is aligned in the direction of the wick axis or about a horizontal axis which is aligned transversely to the direction of the wick axis. For example, said multiple clamping jaws can be arranged in a ring-shaped manner around the wick through opening and consequently around the squeezing region of the wick, as has already been described previously in a general manner in connection with the at least one squeezing element.

The multiple clamping jaws, which are arranged, in particular pivotably hinged, around the squeezing region of the wick, are preferably spaced apart from one another, in particular are uniformly spaced apart from one another in the circumferential direction at a substantially identical gap clearance. The spacing ensures that when the clamping jaws are displaced, they cannot impede one another. As an alternative to this or in addition to it, the multiple clamping jaws, which are arranged around the squeezing region of the wick and are in particular hinged, are each pivotable preferably about a horizontal axis which is aligned transversely to the direction of the wick axis. This produces a design that is simple to produce and manufacture, with which the displacement of the individual clamping jaws can be carried out in a functionally reliable manner.

The squeezing device can additionally comprise an actuating device which is coupled with the at least one squeezing element, by means of which actuating device the squeezing element is displaceable in the direction of the squeezing region of the wick. To this end, reference is additionally made to the statements already made concerning the restoring device, which can consequently also be formed by the actuating device in a dual function.

The actuating device can comprise at least one actuating element which, when the squeezing device is actuated, is displaceable from an initial position, in which the at least one actuating element does not exert any displacement force or at least no significant displacement force on the at least one squeezing element, into an actuating position which causes the at least one squeezing element to move in the direction of the wick squeezing region and the wick squeezing region to be compressed.

Such an actuating element can be realized, in principle, in a wide variety of ways. According to a particularly compact design, which is also simple to realize from a production point of view, in a preferred embodiment the at least one actuating element cooperates with the outside surface of the at least one squeezing element remote from the wick. Here too, there are fundamentally once again multiple possibilities, it being provided in a preferred manner that the at least one actuating element encompasses the at least one squeezing element on the outside surface thereof remote from the wick at least in regions, preferably in a ring-shaped and/or abutting manner at least in regions. As an alternative to this or in addition to it, it can be provided that the at least one actuating element, when it is transferred from the initial position into the actuating position, applies a displacement force onto the outside surface which causes the at least one squeezing element to move. Thus, for example, which will be explained in more detail below, it can be provided in conjunction with a rigid fastening ring as fastening element that said ring is guided along the outside surface of the at least one squeezing element and displaces it from the home position into the squeezing position.

In conjunction with the preferred embodiment already described earlier, where the at least one squeezing element is formed by multiple clamping jaws, it can be provided, for example, that the at least one actuating element encompasses the clamping jaws on the outside surfaces thereof remote from the wick, preferably in a ring-shaped and/or abutting manner, such that the at least one actuating element, when it is transferred from the initial position into the actuating position, applies a displacement force onto the outside surfaces of the clamping jaws which causes the clamping jaws to move. It can thus be provided in conjunction with a rigid actuating ring as fastening element that said rigid actuating ring is guided along the outside surface and then displaces it correspondingly from the home position into the squeezing position.

As already mentioned beforehand simply as an example, according to a particularly preferred specific design it can consequently be provided in a general manner that the at least one actuating element, for example a rigid (in the sense of non-elastic) actuating element, when transferring from the initial position into the actuating position, is guided along the outside surface of the at least one squeezing element and displaces it from the home position into the squeezing position. In order to be able to accomplish this, it can be provided in a preferred manner that the at least one squeezing element comprises, on the outside surface remote from the wick, a displacement contour which interacts with the at least one actuating element when it is displaced from the initial position into the actuating position, such that the at least one squeezing element is displaceable, in particular pivotable, in the direction of the wick.

Such a displacement contour can be formed, for example, by a structure which thickens when viewed in the displacement direction of the actuating element and/or a ramp structure which interacts with the at least one actuating element, when it is displaced from the initial position into the actuating position, by displacing, in particular pivoting, the at least one squeezing element.

Particularly preferred, in this connection, is a specific design where the actuating element is formed by an actuating ring. Such an actuating ring can be realized with little material expenditure in a manner that is simple to produce and manufacture and is additionally distinguished by a particularly high level of functional reliability with reference to the displacement possibility, in particular when it comprises a rounded cross section, for example, in the bearing region or a circular cross section overall because the actuating ring is then reliably prevented from hooking or jamming.

As an alternative to this or where applicable in addition to it, however, it can also be provided that the at least one actuating element is formed by an actuating ring which is elastic at least in regions and encompasses the at least one squeezing element, in particular the clamping jaws as squeezing element, on the outside surface of which remote from the wick in a ring-shaped, in particular ring-shaped and abutting manner, such that when the actuating device is actuated, the actuating ring is decompressed and as a result the ring diameter is modified in the sense of the actuating ring transferring from the initial position into the actuating position such that the at least one squeezing element is displaced from the home position into the squeezing position.

According to a further particularly preferred specific design, the actuating device can further comprise an actuating lever, by means of which the at least one actuating element is displaceable, the actuating lever being pivotably hinged at at least one pivot point on the container or on a component which is fixedly connectable to the container, and wherein the actuating lever comprises an actuating element cooperation point which is at a spacing from the at least one pivot point, to which actuating element cooperation point the actuating element is connected, in particularly is hinged. With such an actuating lever, the squeezing device can be actuated in a particularly simple manner and, additionally, the desired squeezing force can be applied in a simple and rapid manner.

Specifically to this end, the actuating lever can comprise a first L leg and a second L leg, which each comprise a pivot point which, with reference to the container, lies on opposite sides of the container or of a component which is connectable to the container, and each comprise an actuating element cooperation point which lies, with reference to the wick, on opposite sides of the actuating element. The opposite arrangement of two L legs ensures that the squeezing force can be applied onto the wick squeezing region in a functionally secure and reliable manner.

The actuating element cooperation point can be realized in each case on a free end region of a second L leg region of the first and second L leg which projects in an angled manner from a first L leg region. As an alternative to this or in addition to it, the pivot point can be realized and/or arranged on the first and second L leg in the transition region between the first L leg region and the second L leg region. Particularly advantageous lever conditions and consequently force conditions are produced as a result.

It is provided in a preferred manner for common actuation of the two L legs that the actuating lever, which preferably comprises a U form overall or comprises a U-shaped region, comprises a connection element which connects the first and second L legs and can form, for example a U base.

In order to take the relative displacement of the actuating element into consideration, the actuating element cooperation point can be realized as a slide guide where a journal on the actuating element side engages in a slide guide on the actuating lever side and is forcibly guided therein.

The at least one pivot point of the actuating lever, about which it is pivotable, can be formed by a pivot bearing connection where the actuating lever is pivotably mounted indirectly or directly on the container, for example on a wick holding ring which is insertable in the container. The only important factor is a support which is independent of the squeezing device in order to be able to apply a corresponding squeezing force.

According to an alternative embodiment, the displaceable clamping jaws can also be a constituent part of a shearing arrangement which comprises two, preferably two-armed, clamping levers, which are pivotable relative to one another about at least one pivot axis, preferably about at least one vertical axis as pivot axis which is aligned in the direction of the wick axis and, in each case with reference to the pivot axis, each realize or comprise one of the clamping jaws on their one lever side assigned to the squeezing region of the wick in each case, whilst their other lever side remote from the squeezing region of the wick realizes the actuating device or is at least a constituent part of an actuating device. That is to say in other words that the clamping jaws are either an integral constituent part of the clamping lever or else can also be formed by separate components. Such a shear-like arrangement also enables functionally reliable squeezing of the squeezing region of the wick and is also simple to produce and manufacture.

Particularly preferred, in this connection, is a specific design, according to which the clamping levers are coupled with one another by means of a coupling device such that they are displaceable together when they are activated, in particular are displaceable about a common pivot axis as pivot joint. The advantage of this is that a relatively uniform squeezing force acts on the squeezing region, resulting in a reliable boost.

In addition, the clamping lever can be pretensioned into the home position by means of a pretensioning device, preferably by means of at least one spring element, so that the clamping levers and consequently the clamping lever-side clamping jaws are displaceable out of the home position into the squeezing position against the force of the pretensioning device. The pretensioning device then additionally brings about a reliable return of the clamping levers into the home position when the actuating device is no longer actuated or the clamping levers are not acted by means of with force. Particularly preferred is an embodiment where the pretensioning device also realizes the coupling device at the same time in a dual function.

Here too, it is also provided in a preferred manner that the clamping levers are pivotably mounted directly or indirectly on the container or on a wick holding ring which is insertable into the container. The only important factor is a support which is independent of the squeezing device in order to be able to apply a corresponding squeezing force.

As already mentioned previously, it is particularly advantageous when the wick is elastically deformable at least in the squeezing region of the wick such that the squeezing region of the wick can return to its original form again after being acted upon by means of squeezing force and/or after being compressed. In addition, where applicable, the resetting of the at least one squeezing element of the squeezing device can be brought about or at least supported thereby.

Particularly preferred is additionally a design where the substance quantity conveyable in the direction of the substance dispensing region and/or the boost time is predefined by a squeezing force which can be applied to the squeezing region of the wick by means of the squeezing device. This can be effected, for example, by means of a squeezing force adjusting device, by means of which the squeezing force acting on the squeezing region is adjustable. The squeezing force adjusting device can be formed, for example, by a stop element which only permits a certain displacement path of the squeezing element. If said stop element is realized so as to be adjustable or displaceable, different squeezing forces and consequently different boost times can be set. In this case, use is made of the fact that the boost time (which is defined by the time span which the wick requires after a squeezing operation in order to return to the initial or neutral state when the squeezing device is not actuated) depends essentially on the squeezing force applied.

According to a particularly preferred specific design of the device according to the invention, it is provided that the device, in particular a device realized as a vaporizing device, comprises a housing, in and/or on which the at least one heating element is arranged and/or to which the container is connectable, in particular is releasably connectable. This is effected preferably in such a manner that the container is insertable, in particular releasably insertable, into the housing.

In addition, a squeezing device and a method are also claimed. The advantages produced hereby have already been explained in detail previously such that to avoid repetition reference is made to the statements previously made.

The advantageous realizations and further developments of the invention explained above and/or reproduced in the subclaims can be used, in this case—apart from, for example, in cases of clear dependencies or incompatible alternatives—individually or, however, also in arbitrary combinations with one another.

BRIEF DESCRIPTION OF THE SEVERAL VIEWS OF THE DRAWING

The invention and its advantageous realizations and further developments are explained in more detail below by way of simply exemplary and schematic drawings, in which:

FIGS. 4a, 4b shows schematically a schematic sketch, in which the functioning and operating method of the squeezing device according to the invention is explained in more detail as an example, FIG. 4a showing the non-actuated squeezing device whilst FIG. 4b shows the actuated squeezing device and FIGS. 5a, 5b shows schematically a schematic sketch of an alternative embodiment with a clamping lever in a squeezing device comprising a shear arrangement, in which the functioning and operating method is explained in more detail as an example, FIG. 5a showing the non-actuated squeezing device whilst FIG. 5b shows the actuated squeezing device.

DESCRIPTION OF THE INVENTION

Figure 1:
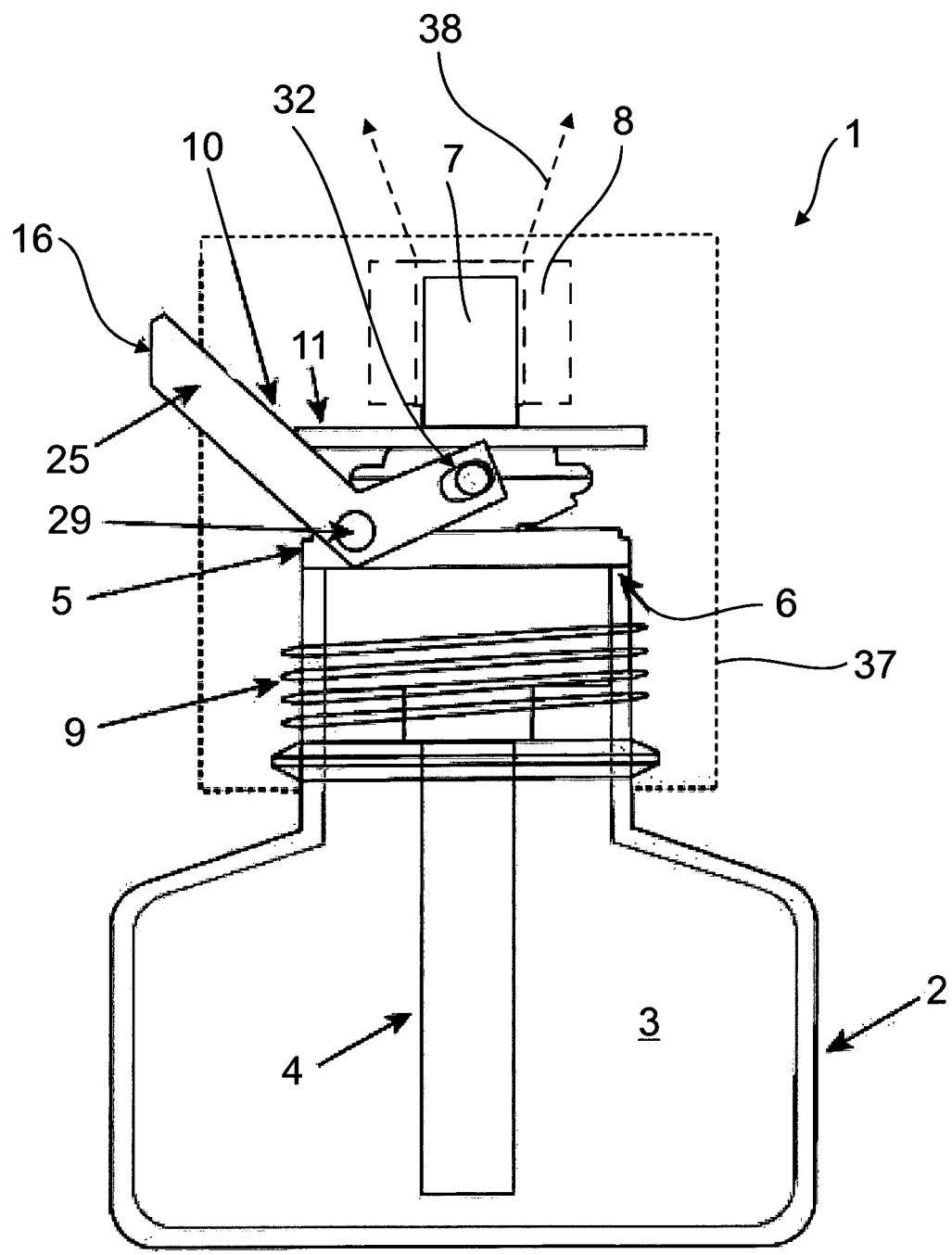
FIG. 1 shows schematically a schematic sketch of an exemplary embodiment according to the invention with a container, a wick arranged in the container projecting beyond the container by way of a free wick end, a heating element assigned to the free wick end and a squeezing device according to the invention.

FIG. 1 shows schematically and as an example a schematic sketch of an exemplary embodiment of a device 1 according to the invention for dispensing, in particular for vaporizing, volatile substances, in particular fragrances and/or active agents. Said device 1 comprises a container 2 in which a substance 3 to be dispensed is received, for example in the form of a liquid.

A wick 4 as capillary element is inserted into the container and is in contact with the substance 3 to be dispensed, the wick 4 being inserted into a container opening 6 of the container 2 by means of a wick holding ring 5. Said wick holding ring 5 (see also FIG. 2) comprises a wick opening (not shown here) which surrounds the wick in a bearing connection.

As can be seen further from FIG. 1, the wick 4 projects beyond the container or the container opening 6 with a free wick end 7 which realizes a substance dispensing region or a substance outlet surface, via which the substance conveyed upward into the region of the free wick end 7 on account of the capillary action of the wick 4 is output into the surrounding area.

To increase the dispensing rate, at least one heating element 8, for example in the form of an electrical heating element, can be assigned to the free wick end 7, as shown purely schematically and by a dotted line in FIG. 1, by means of which heating element the free wick end 7 is heatable to increase the dispensing or vaporizing rate. The heating element 8 can be formed, for example, by a heating block or the like which comprises a recess, notch or through opening, into which the free wick end 7 projects at least with a part region.

The heating element 8 is regularly a constituent part of a vaporizing device which is only shown extremely schematically in FIG. 1, comprises a housing 37 which here is only shown schematically and sketched with a dotted line and into which the container 2 is insertable at least in regions, for example as shown in FIG. 1, can be screwed in by means of a thread 9. The substance can then escape or vaporize into the surrounding area (arrow 38) via at least one outlet opening provided in the housing, preferably in the region of the heating element 8 or of the free wick end 7.

In order to increase the dispensing rate or the vaporizing rate of the substance 3 briefly and to be able to obtain a boost effect, the device 1 is provided with a squeezing device 10, which is described in more detail below, by means of which a squeezing region 13 of the wick 4 (see FIGS. 4*a*, 4*b* in this connection) can be acted on or is compressible transiently by means of a squeezing force for a predetermined, defined short squeezing time such that a substance quantity, which is increased compared to a non-squeezed state, is conveyed in the direction of the free wick end 7 (boost effect).

Figure 2:
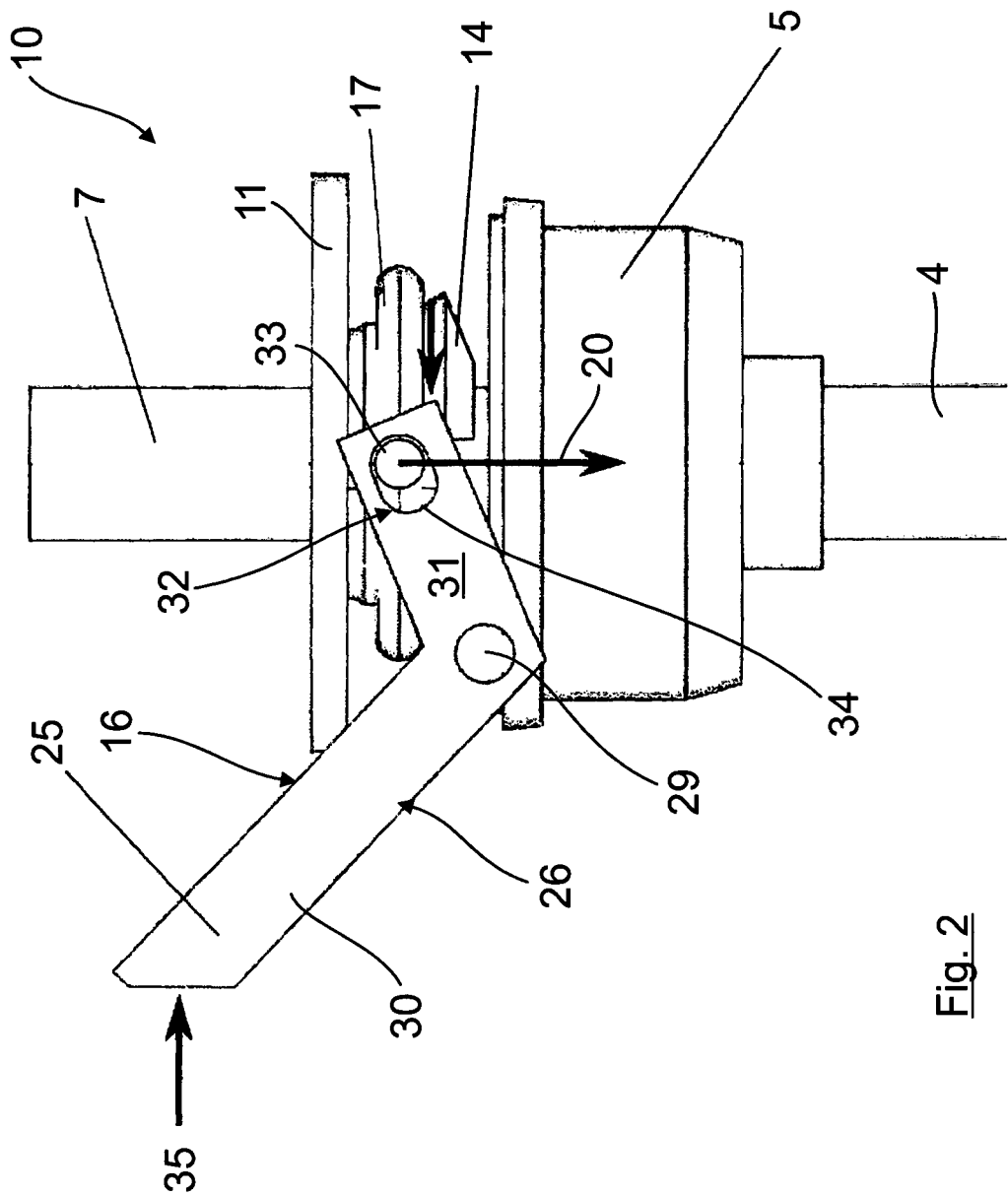
FIG. 2 shows schematically an enlarged view of a detail of an exemplary embodiment of the squeezing device according to the invention.

The squeezing device 10, as can be seen, for example, from an overview of FIGS. 2, 3 and 4*a* to 4*b*, specifically comprises for this purpose a holding ring 11 as holder which comprises a wick through opening 12 via which the wick 4, as shown in FIG. 2 and FIGS. 4*a* and 4*b*, can be guided through or pushed through the holding ring 11 with its free wick end 7.

Multiple clamping jaws 14 are pivotably held on the holding ring 11 around the wick through opening 12 and consequently also around the squeezing region 13 of the free wick end 7 guided through the wick through opening 12. In the example case shown here, there are specifically four clamping jaws 14 (see FIG. 13) which are pivotably mounted on the holding ring 11 so as to pivot around the wick through opening 12, any other number also obviously being possible. Said clamping jaws 14 form a squeezing element of the squeezing device 10 and are pivotable here as an example in a joint region 15 (see FIG. 4*a* and FIG. 4*b*) about a horizontal axis aligned transversely to the direction of the wick axis or are connected in an elastically resilient manner to the holding ring 11 in such a manner that the clamping jaws 14 are pretensioned in the direction of their home position I shown in FIG. 4*a*, such that when there is a lack of force application from the squeezing device 10, the clamping jaws 14 are held in their home position I shown in FIG. 4*a*.

Figure 3:
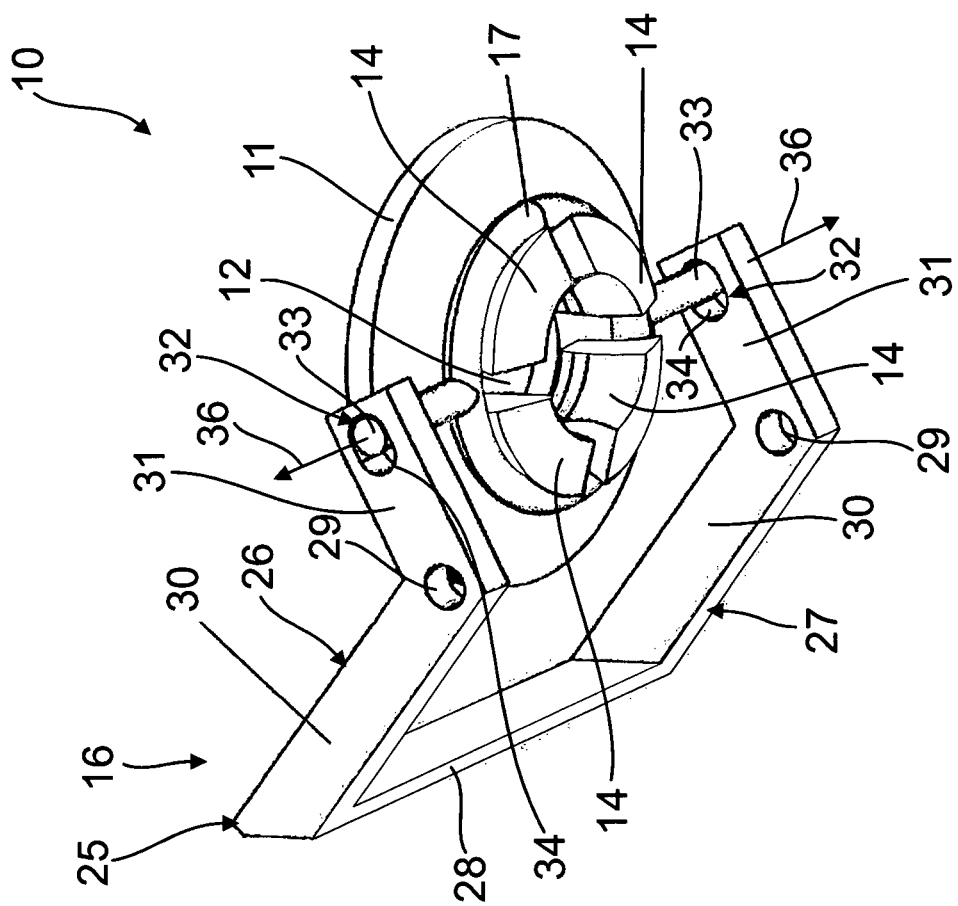
FIG. 3 shows a schematic, perspective bottom view of the exemplary squeezing device according to the invention according to FIG. 2 without a wick.

As can be seen in particular in FIG. 3, the individual clamping jaws 14 can comprise a substantially identical form here and are also spaced uniformly apart from one another.

An actuating device 16, by means of which the clamping jaws 14 are displaceable or pivotable out of their home position I shown in FIG. 4*a* into their squeezing position II shown in FIG. 4*b*, is provided for actuating the squeezing device 10. To this end, the actuating device comprises an actuating element which is realized here simply as an example by an actuating ring 17 which encompasses the clamping jaws in a ring-shaped manner in the home position I shown in FIG. 4*a* and/or in a manner abutting against the outside surface thereof remote from the wick 4.

FIG. 4*a* shows the actuating ring 17 in its initial position A, in which it does not exert any displacement force or any significant displacement force onto the clamping jaws 14. If the actuating ring 17, which can be realized, for example, from a rigid, non-elastic material, for example a plastics material, is then moved downward on actuation of the squeezing device 10 in a manner described in more detail below in arrow direction 18 along the outside surface of the clamping jaws 14 into the actuating position B shown in FIG. 4*b*, then the actuating ring 17 runs onto a displacement structure, realized here as an example by a ramp structure 19, as a result of which the clamping jaws 14 are pivoted about the joint region 15 in the direction of the squeezing region 13 of the wick 4 and, as shown purely in an extremely schematic manner in FIG. 4*b*, the squeezing region 13 is compressed or squeezed such that an increased substance quantity compared to the non-squeezed state (see arrow 20) is displaced briefly and in a boost-like manner substantially in the upward direction toward the free wick end 7.

A squeezing element contact surface 21, realized here simply as an example in a convex manner, with the clamping jaws 14 in said squeezing position II, causes the wick 4 to be acted upon in the squeezing region 13 by means of a force or force component 22 aligned obliquely upward substantially in the direction of the free wick end 7, which favors the boost-like concentration and accumulation of substance 3 in the free wick end 7.

The concave squeezing element contact surface 21 additionally causes the wick 4 to comprise a form here which tapers toward the direct contact region, in particular a form shown here which tapers downward in a cone-like manner in the wick squeezing region 13 and when viewed in the direction of the wick vertical axis, when the squeezing device is actuated, in the direct contact region between the squeezing element contact surface 21 and the wick 4. However, other forms can also be possible as an alternative to the convex design of the squeezing element contact surface, thus, for example, a concave or rectilinear form.

In particular, the form of the wick squeezing region 13 which tapers in a cone-like manner or obliquely downward promotes the boost effect because, as a result, the substance accumulated in the region of the wick or of the free wick end 7 is pumpable or conveyable upward in a targeted manner toward the widening free wick end 7.

If, as shown in FIG. 4*a* and FIG. 4*b*, the end face 24 connecting to the squeezing element contact surface 21 on the one side or the ramp structure 19 on the opposite side is flattened in a step-shaped manner, a wick region 23 which widens in a step-like or edge-like manner is produced, as can be seen in FIG. 4*b*, when viewed in the direction of the wick vertical axis below the direct contact region between the clamping jaws 14 and the wick 4, which wick region, on account of the abrupt transition from a constriction to a widening, can also promote the boost-like brief concentration for increasing the substance and the conveying thereof in the direction of the widening free wick end 7.

If an increased quantity of substance 3 to be dispensed is then situated in the region of the free wick end 7 due to the boost effect brought about by the squeezing device 10, more vaporization can then also be carried out there briefly, which results in the desired increased dispensing or vaporizing rate.

For displacing the actuating ring 17 between the initial position A and the actuating position B, the actuating device 16 further includes an actuating lever 25, which here is U-shaped purely as an example and comprises a first L leg 26 and a second L leg 27 which is spaced therefrom and is constructed in a substantially identical manner, the two legs being connected together by a U base 28 as connection element.

As can be seen in particular from the overall view of FIGS. 1 to 3, the two parallel extending first and second L legs 26, 27 lie on opposite sides of the wick 4 or of the container opening 6 and are pivotably hinged there in each case on the wick holding ring 5 at a pivot point 29 such that for actuating the actuating ring 17, the actuating lever 25 is pivotably hinged on the wick holding ring 5 and consequently indirectly on the container 2 so as to be pivotable by means of the two oppositely situated pivot points 29.

As can be seen further additionally from FIGS. 1 to 3, the two L legs 26, 27 each comprise on a free end region of a second L leg region 31, which projects in an angular manner from a first L leg region 30, in each case an actuating ring cooperation point which is realized as a slide guide 32, where a journal 33 on the actuating ring side engages in a slide guide 34 on the actuating lever side and is forcibly guided therein such that the actuating ring 17, when the actuating lever 25 pivots about the pivot points 29 which are located here, as an example, precisely in the transition region between the first L leg region 30 and the second L leg region 31, is displaced, as a result of the application of a force 35 (see FIG. 2) in a forcibly guided manner, by the slide guide 32 out of the initial position A shown in FIG. 4a into the actuating position B shown in FIG. 4b, such that, consequently, the clamping jaws 14 are also displaced out of their home position I shown in FIG. 4a into their squeezing position II shown in FIG. 4b (see also displacement arrow 18 in FIG. 2 in this respect).

If, after the boost brought about in this manner by the squeezing of the wick 4 in the wick squeezing region 13, the actuating lever 25 is released again, the squeezing region 13 is able to be restored and consequently released in various ways:

thus, on the one hand, as a result of the operator moving the actuating lever 25 back and, in addition to this or as an alternative to it, as a result of the elastic resilience of the wick squeezing region 13 and/or as a result of the elastically resilient connection of the clamping jaws 14 in the joint region 15 in such a manner that said clamping jaws 14, connected in an elastically resilient manner to the holding ring 11, move back again substantially automatically from the squeezing position II into the home position I and, as already stated, as a result of their elastically resilient connection, where the clamping jaws 14 are connected to the holding ring 11 pretensioned in the direction of the home position I. The restoring force would then have to be designed here such that the clamping jaws 14, in the event of a lack of force application on the actuating lever 25, could also transfer the actuating ring 17 automatically from the actuating position B into the initial position A.

As an alternative to the realization variant described here with an actuating ring 17 which is displaced along the outside surface of the clamping jaws 14 and is preferably produced from a solid, non-elastic material, the actuating ring 17 could also be produced from an elastic material. In said case, the actuating device 16, as only shown extremely schematically in FIG. 3 in connection with the force cooperation arrows 36, could then comprise an actuating element which cooperates with the journal 33 in the direction of the force cooperation arrow 36 and consequently decompresses the actuating ring 17 and stretches it such that said actuating ring exerts a displacement force onto the clamping jaws 14 in order to transfer them from their home position I into the squeezing position II. Were the journals 33 then to be released again, the elastic actuating ring 17 would move back automatically into its initial position and correspondingly bring about a return of the clamping jaws from the squeezing position II into the home position I, which can also be effected once again in the manner described previously, for example automatically as a result of the elastically resilient connection of the clamping jaws 14, pretensioned in the direction of the home position I, in the joint region 15 on the holding ring 11 and/or as a result of the elastic resilience of the wick squeezing region 13 and/or as a result of the operator moving the actuating ring 17 back.

FIGS. 5a and 5b show schematically a schematic sketch of an alternative embodiment of a clamping lever 39, 40 in a squeezing device 10 which comprises a shear arrangement, in which the modes of functioning and operating are explained in more detail, purely as an example. In this connection, FIG. 5a shows the non-actuated squeezing device 10, whilst FIG. 5b shows the actuated squeezing device 10.

The design of the device 1 can be fundamentally identical to that which has been described previously in connection with the realization variants described as an example, that is to say that the device 1, here too, comprises a container 2 in which a substance 3 to be dispensed, for example in the form of a liquid, is received.

A wick 4, as capillary element, is inserted into the container and said wick is in contact with the substance 3 to be dispensed, the wick 4 being inserted into a container opening 6 of the container 2 here by means of a wick holding ring 5. Said wick holding ring 5 (see also FIG. 2) comprises a wick opening which is not shown here and surrounds the wick in a bearing connection.

Here too, the wick 4 projects beyond the container or the container opening 6 by way of a free wick end 7 which realizes the substance dispensing region or a substance outlet surface, via which the substance conveyed upward on account of the capillary action of the wick 4 into the region of the free wick end 7 is dispensed into the surrounding area.

To increase the dispensing rate, at least one heating element 8, for example in the form of an electrical heating element, can be assigned, here too, to the free wick end 7, as shown purely schematically and by a dotted line in FIG. 1, by means of which heating element the free wick end 7 is heatable to increase the dispensing or vaporizing rate.

The heating element 8, here too, can also be a constituent part of a vaporizing device, only shown extremely schematically in FIG. 1, which comprises a housing 37 into which the container 2 is insertable at least in regions, for example as shown in FIG. 1 can be screwed in by means of a thread 9. The substance can then escape or vaporize into the surrounding area (arrow 38) via at least one outlet opening provided in the housing, preferably in the region of the heating element 8 or of the free wick end 7.

The difference to the embodiments described previously is in the specific design of squeezing device 10, the clamping jaws 14 of which are a constituent part of a shear arrangement which comprises two clamping levers 39, 40 which are pivotable relative to one another about a pivot axis 31, which realizes a pivot or rotary joint, preferably about a vertical axis as pivot axis which is aligned in the direction of the wick axis. Said clamping levers 39, 40 realize in each case one of the clamping jaws 14 on their first lever side 42, with reference to the pivot axis 41, which is assigned to the squeezing region 13 of the wick 4, whilst their second lever side 43, remote from the squeezing region 13 of the wick 4, realizes the actuating device or is at least a constituent part of an actuating device, which is, however, not shown any further here.

The clamping levers 39, 40 are pretensioned by means of a pretensioning device, formed here as an example by at least one spring element 44, into the home position I shown in FIG. 5a. In order to displace the clamping levers 39, 40 and consequently the clamping jaws 14 on the clamping lever side into the squeezing position II, the ends of the second lever side 43 have to be pivoted from the home position I into the squeezing position II against the force of the pretensioning device or of the spring element 44.

In a preferred manner, at the same time the pretensioning device also realizes a coupling device which ensures that the clamping levers 39, 40 are displaceable together.

In addition, the spring element 44 or the pretensioning device once again causes the clamping levers 39, 40 and consequently the clamping jaws 14 to return in a reliable manner to the home position I when the actuating device or the second lever side 43 of the clamping levers 39, 40 is no longer actuated or no longer acted upon by means of force.

Here too, it is once again provided in a preferred manner that the clamping levers 39, 40 are pivotably mounted indirectly or directly on the container 2 or on the wick holding ring 5 which is insertable into the container 2.

In the case of all embodiments described previously, it is provided that in the home position I, the clamping jaws 14 are at a defined gap clearance from the squeezing region 13 of the wick 4, as a result of which air is able to flow around the wick 4.

The invention claimed is:

1. A device for dispensing volatile substances, the device comprising:
   a container for receiving a substance to be dispensed;
   at least one wick forming a capillary element in contact with the substance to be dispensed, said at least one wick being arranged at least partly in said container and said at least one wick having a substance dispensing region;
   a heating element assigned to said wick;
   a squeezing device assigned to said wick, said squeezing device having at least one squeezing element disposed to subject a squeezing region of said wick to a squeezing force for causing a defined substance quantity to be conveyed substantially in the direction of the substance dispensing region of said wick; and
   said at least one squeezing element being arranged on said squeezing device so as to be displaceable between a home position and a squeezing position;
   said squeezing device having an actuating device being coupled with said at least one squeezing element, and being configured to displace said at least one squeezing element in the direction of said squeezing region of said wick to said squeezing position;
   said squeezing device having a restoring element configured to displace said at least one squeezing element from the squeezing position back into the home position; and
   said restoring element being formed by an elastically resilient element which is compressible when said at least one squeezing element is transferred into the squeezing position and which, when there is a lack of force application by said squeezing device and/or said squeezing device is not actuated, said at least one squeezing element is configured to move automatically from the squeezing position back into the home position.

2. The device according to claim 1, wherein the substance dispensing region is formed by a free wick end which projects beyond said container, and wherein said squeezing device is assigned to said wick at said free wick end such that said squeezing region of said wick is defined at said free wick end.

3. The device according to claim 1, wherein said at least one squeezing element is disposed with a gap clearance from the squeezing region of said wick in the home position.

4. The device according to claim 1, wherein, when said squeezing device is actuated, said at least one squeezing element, which is pivotally connected to said squeezing device, in a state thereof pivoted into the squeezing position, abuts by way of a squeezing element contact surface against the wick squeezing region in a bearing connection.

5. The device according to claim 4, wherein said at least one squeezing element is arranged so as to be pivotable, in such a manner and/or in that the squeezing element contact surface comprises such a design and form that the wick in the wick squeezing region is acted upon by a force which acts substantially in the direction of the substance dispensing region.

6. The device according to claim 4, wherein said squeezing element contact surface is configured with a design and form that said wick, in the wick squeezing region and when viewed in the direction of a wick vertical axis, comprises a form, in a direct contact region between the squeezing element contact surface and said wick when said squeezing device is actuated, which tapers at least in regions of said form toward the direct contact region, and wherein the wick region, which connects between said at least one squeezing element and said wick in the direction of the wick vertical axis below the direct contact region, widens with a step or with an edge.

7. The device according to claim 1, wherein a restoring element of said restoring device is realized by an elastically resilient squeezing region of said wick and/or is realized by an elastically resilient connection between said at least one squeezing element and said squeezing device, where said at least one squeezing element, pre-tensioned in the direction of the home position, is connected in an elastically resilient manner to said squeezing device in such a manner that said at least one squeezing element, when there is a lack of force application by said squeezing device and/or said squeezing device is not actuated, moves automatically from the squeezing position back into the home position.

8. The device according to claim 1, wherein said squeezing device is formed with a wick through opening through which said wick is guided and where said at least one squeezing element assigned to the squeezing region of said wick.

9. The device according to claim 8, wherein said at least one squeezing element is arranged at least in regions around said wick through opening and consequently around said squeezing region of said wick.

10. The device according to claim 8, wherein:
    said wick through opening is formed in a plate-shaped or ring-shaped, holder of said squeezing device, and
    said at least one squeezing element is pivotably mounted at least in regions around said wick through opening and consequently around said squeezing region of said wick on said holder of said squeezing device.

11. The device according to claim 1, wherein said squeezing element is formed by a plurality of displaceable clamping jaws.

12. The device according to claim 11, wherein said plurality of clamping jaws are pivotably mounted about a vertical axis that is aligned in a direction of a wick axis or about a horizontal axis which is aligned transversely to the direction of the wick axis.

13. The device according to claim 11, wherein said plurality of clamping jaws which are pivotally hinged around said squeezing region of said wick, are spaced apart from one another in a circumferential direction at an identical gap clearance, and/or are each pivotable about a horizontal pivot axis that is aligned transversely to the direction of the wick axis.

14. The device according to claim 1, wherein said actuating device comprises at least one actuating element which, when said squeezing device is actuated, is displaceable from an initial position, in which said at least one actuating element does not exert any displacement force on said at least one squeezing element, into an actuating position which causes said at least one squeezing element to move in the direction of said wick squeezing region and said wick squeezing region to be compressed.

15. The device according to claim 14, wherein said at least one actuating element is disposed to cooperate with an outer surface of said at least one squeezing element remote from said wick, such that:
said at least one actuating element encompasses said at least one squeezing element on the outer surface thereof remote from said wick at least in regions; and/or
said at least one actuating element, upon being moved from the initial position into the actuating position, applies a displacement force onto the outer surface which causes said at least one squeezing element to move.

16. The device according to claim 11, wherein an at least one actuating element encompasses said clamping jaws on the outside surfaces thereof remote from said wick, such that said at least one actuating element, upon being moved from the initial position into the actuating position, applies a displacement force onto the outer surfaces of said clamping jaws which causes said clamping jaws to move.

17. The device according to claim 14, wherein said at least one actuating element is a rigid actuating element configured, when transferring from the initial position into the actuating position, to be guided along the outside surface of said at least one squeezing element and to displace the squeezing element from the home position into the squeezing position, wherein said at least one squeezing element has, on an outside surface remote from said wick, a displacement contour which interacts with said at least one actuating element when it is displaced from the initial position into the actuating position such that said at least one squeezing element is pivotally displaceable in a direction of the wick.

18. The device according to claim 17, wherein said displacement contour is formed by a structure which thickens when viewed in the displacement direction of said actuating element and/or a ramp structure which interacts with said at least one actuating element, when it is displaced from the initial position into the actuating position by pivoting said at least one squeezing element.

19. The device according to claim 17, wherein said actuating element is an actuating ring.

20. The device according to claim 14, wherein said at least one actuating element is an actuating ring which is elastic at least in regions and encompasses said at least one squeezing element on an outer surface thereof remote from said wick in a ring-shaped such that when said actuating device is actuated, said actuating ring is decompressed and as a result a ring diameter is modified in the sense of the actuating ring transferring from the initial position into the actuating position such that said at least one squeezing element is displaced from the home position into the squeezing position.

21. The device according to claim 14, wherein:
said actuating device further comprises an actuating lever, by means of which said at least one actuating element is displaceable;
said actuating lever is pivotably hinged at at least one pivot point on said container or on a component which is fixedly connectable to said container; and
said actuating lever comprises at least one actuating element cooperation point which is at a spacing from the pivot point, to which actuating element cooperation point the actuating element is connected.

22. The device according to claim 21, wherein said actuating lever comprises a first L leg and a second L leg which each comprises a pivot point which, with reference to said container, lies on opposite sides of said container or of a component connected to said container, and each comprises an actuating element cooperation point which lies, with reference to said wick, on opposite sides of said actuating element.

23. The device according to claim 21, wherein said actuating element cooperation point is disposed in each case on a free end region of a second L leg region of said first L leg and of said second L leg which projects in an angled manner from a first L leg region and/or in that said pivot point is disposed and/or arranged on said first L leg and second L leg in a transition region between said first L leg region and said second L leg region.

24. The device according to claim 23, wherein said actuating lever, which is U shaped or which includes a U-shaped region, comprises a connection element which connects said first L leg and second L leg to form a U base.

25. The device according to claim 21, wherein said actuating element cooperation point is a slide guide where a journal on an actuating element side engages in a further slide guide on said actuating lever side and is forcibly guided therein.

26. The device according to claim 21, wherein said at least one pivot point of said actuating lever, about which said lever is pivotable, is formed by a pivot bearing connection where said actuating lever is pivotably mounted indirectly or directly on said container or on a wick holding ring which is insertable into said container.

27. The device according to claim 11, wherein said displaceable clamping jaws are a constituent part of a shearing arrangement which comprises two clamping levers, which are pivotable relative to one another about at least one vertical pivot axis that is aligned in the direction of the wick axis and, in each case with reference to said pivot axis, and each realize or comprise on their one lever side assigned to the squeezing region of said wick in each case one of said clamping jaws, while their other lever side remote from the squeezing region of said wick realizes said actuating device or a constituent part of said actuating device.

28. The device according to claim 27, wherein said clamping levers are coupled with one another by way of a coupling device to cause said clamping levers to be displaceable together when they are activated, in particular displaceable about a common pivot axis as pivot joint.

29. The device according to claim 27, wherein said clamping lever is pretensioned into the home position by a pretensioning device being at least one spring element, so that said clamping levers and consequently the clamping lever-side clamping jaws are displaceable out of the home position into the squeezing position against a force of said pretensioning device.

30. The device according to claim 27, wherein said clamping levers are pivotably mounted directly or indirectly on said container or on a wick holding ring that is insertable into said container.

31. The device according to claim 1, wherein said wick is elastically deformable at least in the squeezing region of said wick such that the squeezing region of said wick returns into an original shape after being acted upon with a squeezing force and/or after being compressed.

32. The device according to claim 1, wherein a substance quantity conveyable in the direction of said substance dispensing region and/or a boost time of said wick is predefined by the squeezing force that can be output onto said squeezing region of said wick by way of said squeezing device, and wherein a squeezing force adjusting device is configured to enable adjustment of the squeezing force acting on said squeezing region.

33. The device according to claim 1, configured as a vaporizing device comprising a housing, in and/or on which the at least one heating element is arranged and/or to which the container is releasably connectable, wherein said container is releasably insertable into said housing.

34. A squeezing device for the device according to claim 1, the squeezing device comprising: at least one squeezing element for acting on, or compressing, an elastically deformable squeezing region of a wick, briefly and/or transiently, by way of a squeezing force.

* * * * *